(12) United States Patent
Shambayati

(10) Patent No.: US 9,333,346 B1
(45) Date of Patent: May 10, 2016

(54) MULTI-MODE MICROCURRENT STIMULUS SYSTEM WITH SAFETY CIRCUITRY AND RELATED METHODS

(71) Applicant: TAMA Research Corp., Phoenix, AZ (US)

(72) Inventor: Ali Shambayati, Phoenix, AZ (US)

(73) Assignee: TAMA Research Corp., Phoenix, AZ (US)

( * ) Notice: Subject to any disclaimer, the term of this patent is extended or adjusted under 35 U.S.C. 154(b) by 0 days.

(21) Appl. No.: 14/283,125

(22) Filed: May 20, 2014

Related U.S. Application Data

(63) Continuation of application No. 13/541,583, filed on Jul. 3, 2012, now Pat. No. 8,731,657.

(60) Provisional application No. 61/504,601, filed on Jul. 5, 2011.

(51) Int. Cl.
*A61N 1/36* (2006.01)

(52) U.S. Cl.
CPC ........ *A61N 1/36014* (2013.01); *A61N 1/36003* (2013.01)

(58) Field of Classification Search
None
See application file for complete search history.

(56) References Cited

U.S. PATENT DOCUMENTS

| | | | | |
|---|---|---|---|---|
| 3,902,502 | A * | 9/1975 | Liss et al. | 607/46 |
| 4,088,141 | A * | 5/1978 | Niemi | 607/63 |
| 4,541,432 | A | 9/1985 | Molina-Negro et al. | |
| 4,823,797 | A * | 4/1989 | Heinze et al. | 600/481 |
| 4,989,605 | A | 2/1991 | Rossen | |
| 5,395,398 | A | 3/1995 | Rogozinski | |
| 5,476,481 | A * | 12/1995 | Schondorf | 607/2 |
| 5,522,864 | A | 6/1996 | Wallace et al. | |
| 5,573,552 | A | 11/1996 | Hansjurgens | |
| 5,578,060 | A | 11/1996 | Pohl et al. | |
| 5,800,477 | A | 9/1998 | Groux | |
| 5,817,138 | A | 10/1998 | Suzuki | |
| 5,935,156 | A | 8/1999 | Chandler et al. | |
| 6,026,329 | A | 2/2000 | Che et al. | |
| 6,035,236 | A | 3/2000 | Jarding et al. | |
| 6,275,735 | B1 | 8/2001 | Jarding et al. | |
| 6,408,211 | B1 | 6/2002 | Powell | |
| 6,606,519 | B2 | 8/2003 | Powell | |
| 6,745,078 | B1 * | 6/2004 | Buchner | 607/72 |
| 7,158,834 | B2 | 1/2007 | Paul, Jr. | |
| 7,317,948 | B1 * | 1/2008 | King et al. | 607/62 |
| 2003/0149420 | A1 * | 8/2003 | Richter | 604/500 |
| 2005/0137649 | A1 * | 6/2005 | Paul, Jr. | 607/53 |
| 2007/0106342 | A1 * | 5/2007 | Schumann | 607/46 |
| 2008/0015657 | A1 * | 1/2008 | Haefner | 607/62 |
| 2008/0249587 | A1 | 10/2008 | Cho et al. | |
| 2009/0043188 | A1 * | 2/2009 | Rauscher | 600/409 |
| 2009/0112283 | A1 | 4/2009 | Kriksunov et al. | |
| 2009/0270788 | A1 | 10/2009 | Marenus et al. | |
| 2010/0105285 | A1 | 4/2010 | Shao | |
| 2010/0274329 | A1 * | 10/2010 | Bradley et al. | 607/90 |
| 2012/0226200 | A1 * | 9/2012 | Wagner et al. | 601/2 |

\* cited by examiner

*Primary Examiner* — Kennedy Schaetzle
(74) *Attorney, Agent, or Firm* — Booth Udall Fuller, PLC

(57) ABSTRACT

A microcurrent stimulation device with a power supply, two or more electrodes electronically coupled to the power supply, a microcontroller configured to generate an electromagnetic waveform, an impedance measurement module configured to measure electrical impedance of one or more biological tissues between the two or more electrodes. A first safety circuit monitors electric current flow through one or more components of the microcurrent stimulation device and interrupts electric current flow if the electric current flow through the one or more components is above a predetermined level. A second safety circuit interrupts electric current flow through the one or more components if a firmware failure occurs.

20 Claims, 12 Drawing Sheets

MULTI-MODE MICROCURRENT STIMULUS SYSTEM WITH SAFETY CIRCUITRY AND RELATED METHODS

CROSS REFERENCE TO RELATED APPLICATIONS

This application is a continuation of the earlier U.S. patent application No. 13/541,583, entitled "Multi-Mode Microcurrent Stimulus System with Safety Circuitry and Related Methods" to Ali Shambayati et al. filed Jul. 3, 2012, now pending, which application claims the benefit of the filing date of U.S. Provisional Patent Application No. 61/504,601, entitled "Multi-Mode Microcurrent Apparatus" to Ali Shambayati et al., which was filed on Jul. 5, 2011, the disclosures of which are hereby incorporated entirely by reference herein.

BACKGROUND

1. Technical Field

Aspects of this document relate to a microcurrent stimulus apparatus that supplies electrical pulses of various shapes and frequencies for the purpose of rejuvenating the skin and toning the underlying muscle for aesthetic purposes.

2. Background Art

Many methods have been developed to provide a more youthful look for the face and body, one of which is electrical stimulation of the skin and/or muscle in an attempt to help tone the skin and/or muscle to reduce the appearance of wrinkles as well as the effects of aging. These devices are commonly known as microcurrent stimulators, which are a subset of electrical muscle stimulators (EMS) or transcutaneous electrical nerve stimulators (TENS). Microcurrent stimulators use electrical currents that are lower than that of a TENS unit.

Microcurrent devices that are presently on the market are available in two form factors: tabletop units, which require administration by trained professionals; and handheld units that are sold through various channels directly to the end user. Most of these devices generally use similar waveforms and therefore produce similar results. Some have fixed electrodes, which limits reaching the tendons of the muscle. Others have limited effectiveness due to the shape of the stimulus pulse. Most products operate in open-loop mode, leaving it to the end user to determine if the muscle has reached its optimum state. As a result, users may over-stimulate their tissue, causing either browning of the skin (burning) or muscle fatigue.

So as to reduce the complexity and length of the Detailed Specification, and to fully establish the state of the art in certain area of technology. Applicant(s) herein expressly incorporate(s) by reference all of the following materials identified in each numbered paragraph below.

U.S. Pat. No. 4,541,432 to Pedro Molina-Negro et al., issued Sep. 17, 1985.

U.S. Pat. No. 4,989,605 to Rossen, issued Feb. 5, 1991.

U.S. Pat. No. 5,395,398 to Rogozinski, issued Mar. 7, 1995.

U.S. Pat. No. 5,522,864 to Wallace et al., issued Jun. 4, 1996.

U.S. Pat. No. 5,573,552 to Hansjurgens, issued Nov. 12, 1996.

U.S. Pat. No. 5,578,060 to Pohl et al., issued Nov. 26, 1996.

U.S. Pat. No. 5,800,477 to Groux, issued Sep. 1, 1998.

U.S. Pat. No. 5,817,138 to Suzuki, issued Oct. 6, 1998.

U.S. Pat. No. 5,935,156 to Chandler et al., issued Aug. 10, 1999.

U.S. Pat. No. 6,026,329 to Che et al., issued Feb. 15, 2000.

U.S. Pat. No. 6,035,236 to Jarding et al., issued. Mar. 7, 2000.

U.S. Pat. No. 6,275,735 to Jarding et al., Aug. 14, 2001.

U.S. Pat. No. 6,408,211 to Powell, issued Jun. 18, 2002.

U.S. Pat. No. 6,606,519 to Powell, issued Aug. 12, 2003.

U.S. Pat. No. 7,158,834 to Paul, Jr., issued Jan. 2, 2007.

U.S. Publication 2008/0249587 to Cho et al., published Oct. 9, 2008.

U.S. Publication 2009/0112283 to Kriksunov et al., published Apr. 30, 2009.

U.S. Publication 2009/0270788 to Marenus et al., published Oct. 29, 2009.

U.S. Publication 2010/0105285 to Shao, Apr. 29, 2010.

Applicants believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

SUMMARY

Implementations of a microcurrent stimulation device may comprise a power supply, two or more electrodes electronically coupled to the power supply, a microcontroller configured to generate an electromagnetic waveform, at impedance measurement module configured to measure electrical impedance of one or more biological tissues between the two or more electrodes, a first safety circuit configured to monitor electric current flow through one or more components of the microcurrent stimulation device and interrupt electric current flow if the electric current flow through the one or more components is above a predetermined level, and a second safety circuit configured to interrupt electric current flow through the one or more components if a firmware failure occurs.

Particular implementations may comprise one or more of the following features. The power supply may be configured to provide an adjustable alternating current (AC) having an upper limit of about 500 micro-Amperes. The microcontroller may be further configured to generate a plurality of electromagnetic waveforms of both high and low varying frequencies. The microcontroller may be further configured to generate a plurality of electromagnetic waveforms of both high and low frequencies of varying amplitudes. The device may be further configured to adjust at least one of a frequency and amplitude of the electromagnetic waveform generated by the microcontroller in response to the measured electrical impedance of the one or more biological tissues between the two or more electrodes. The device may further comprise a memory configured to store information related to one or more physiological characteristics of the one or more biological tissues and wherein the microcurrent stimulation device is further configured to determine a frequency and amplitude of the electromagnetic waveform based at least partly on the stored information. The device may further comprise at least one of a wireless transmitter and a wireless receiver configured to transmit or receive data from an external computer. The device may further comprise two or more electrically isolated channels configured to electrically stimulate biological tissues located at different body locations. The device may further comprise a light emitting diode (LED) or laser. The LED or laser may be configured to emit light from as probe. The device may further comprise, a plurality of probes, each emitting light having a different wavelength. The device may further comprise a plurality of probes configured to form a tweezer.

Implementations of a method of microcurrent stimulation may comprise electronically coupling two or more electrodes to a power supply, generating an electromagnetic waveform using a microcontroller, measuring electrical impedance of one or more biological tissues between the two or more electrodes using an impedance measurement module, monitoring electric current flow through one or more electronic components using a first safety circuit and interrupting electric current flow if the electric current flow through the one or more components is above a predetermined level, and interrupting electric current flow through the one or more components using a second safety circuit if a firmware failure occurs.

Particular implementations may comprise one or more of the following features. The power supply may be configured to provide an adjustable alternating current (AC) having an upper limit of about 500 micro-Amperes. The method may further comprise generating a plurality of electromagnetic waveforms of both high and low varying frequencies using the microcontroller. The method may further comprise generating a plurality of electromagnetic waveforms of both high and low frequencies of varying amplitudes using the microcontroller.

The method may further comprise adjusting at least one of a frequency and amplitude of the electromagnetic waveform generated by the microcontroller in response to the measured electrical impedance of the one or more biological tissues between the two or more electrodes. The method may further comprise storing in memory information related to one or more physiological characteristics of the one or more biological tissues and determining a frequency and amplitude of the electromagnetic waveform based at least partly on the stored information. The method may further comprise transmitting data to an external computer using a wireless transmitter and receiving data from an external computer using a wireless receiver. The method may further comprise generating an electromagnetic waveform through two or more electrically isolated channels configured to electrically stimulate biological tissues located at different body locations. The method may further comprise emitting light from a light emitting diode (LED) or laser. The light may be emitted from a probe. The light may be emitted from a plurality of probes, each probe emitting light having a different wavelength. A plurality of probes may be configured to form a tweezer.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112, ¶6. Thus, the use of the words "function," "means" or "step" in the Description, Drawings, or Claims is not intended to somehow indicate a desire to invoke the special provisions of 35 U.S.C. § 112, ¶6, to define the invention. To the contrary, if the provisions of 35 U.S.C. § 112, ¶6 are sought to be invoked to define the claimed disclosure, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112, ¶6. Moreover, even if the provisions of 35 U.S.C. § 112, ¶6 are invoked to define the claimed disclosure, it is intended that the disclosure not be limited only to the specific structure, material or acts that are described in the preferred embodiments, but in addition, include any and all structures, materials or acts that perform the claimed function as described, in alternative embodiments or forms of the invention, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

DESCRIPTION

This disclosure, its aspects and implementations, are not limited to the specific components, frequency examples, or methods disclosed herein. Many additional components and assembly procedures known in the art consistent with a method and system for microcurrent stimulation of biological tissues are in use with particular implementations from this disclosure. Accordingly, for example, although particular implementations are disclosed, such implementations and implementing components may comprise any components, models, versions, quantities, and/or the like are known in the art for such systems and implementing components, consistent with the intended operation.

Implementations of the systems and methods described herein are aimed at overcoming the above mentioned issues in order to provide the user with an effective and user-friendly product for muscle toning and rejuvenation of the skin, such as tightening the skin and reducing wrinkles, thus resulting in a youthful look and healthier composition.

Figure 1A:
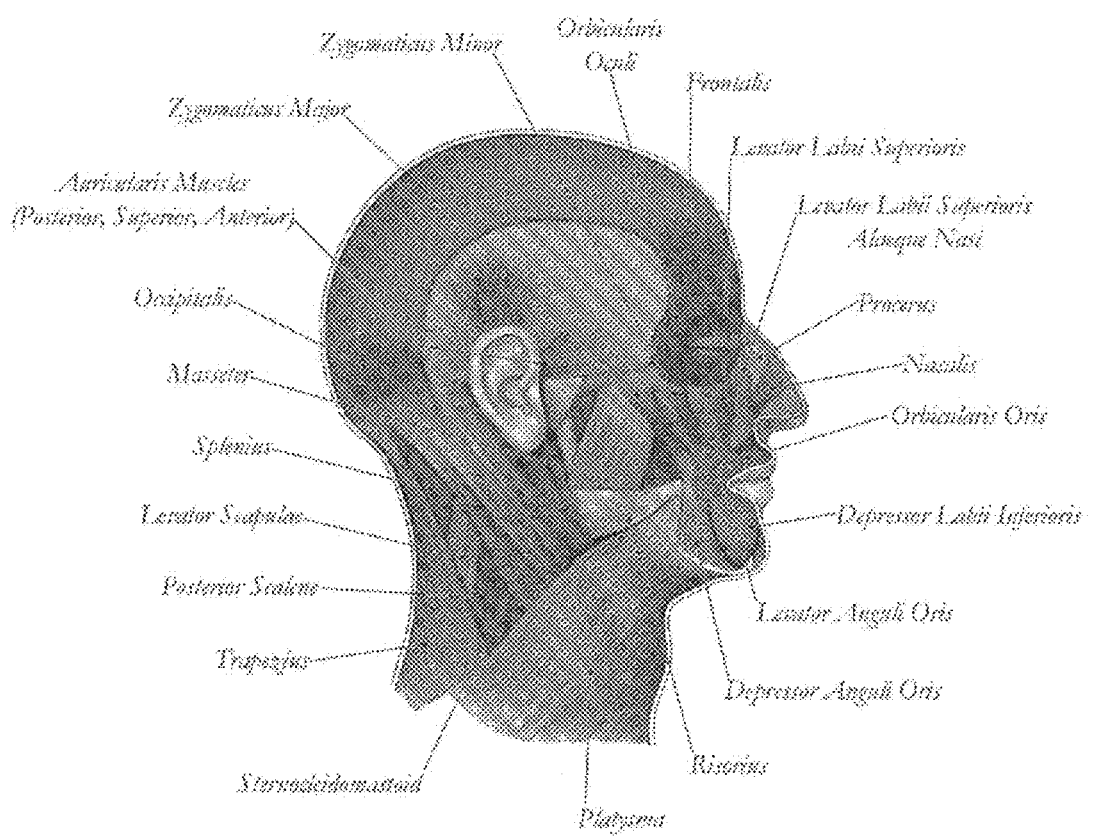
FIGS. 1A-C provide a diagram and various view of facial muscle tissues.
Figure 1B:
Figure 1C:
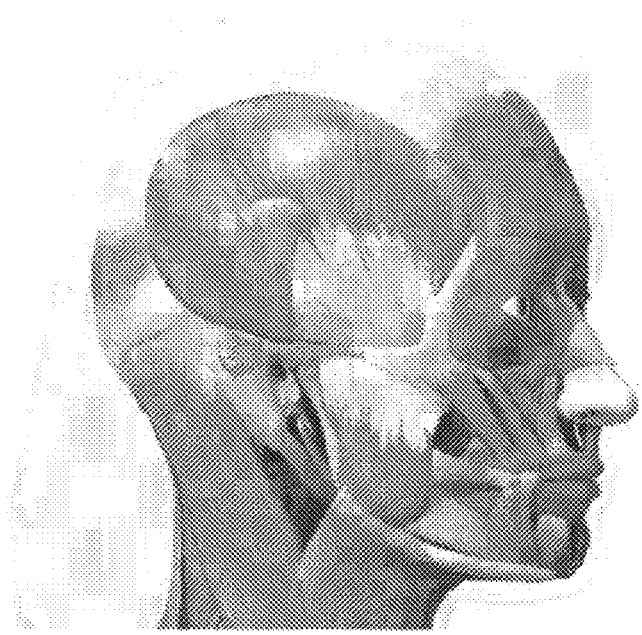

Generally accepted methodologies of microcurrent stimulation rely on currents at or below 500 microamperes that mimic the body's own signals, but this disclosure is not intended to be limited to such current levels. Higher frequency pulses may penetrate deep into the skin tissue and reach the underlying muscle fibers. FIG. 1A provides a labeled diagram of various facial muscles while FIGS. 1B-C provide front and side views of the facial muscles, respectively. The underlying muscle fibers deliver the microcurrent signals to the tendons, thus releasing adenosine triphosphate (ATP) and effectively tightening the muscle and the skin. Lower frequency pulses affect surface tissues more readily. The electric current causes an increase in blood flow in the blood vessels immediately below the area that is being stimulated, thus providing more nutrients to the skin cells during treatment. It also causes an increase in the production of collagen, a group of naturally occurring proteins, which in turn reinforce the muscle tissue. Coupling the microcurrent pulses with light such as, for example, red light, may have the added benefit of heating the tissue, thus further increasing the blood flow, as well as reducing inflammation and healing scars. This, implementations of the multi-mode pulse output of the microcurrent stimulator may simultaneously tone the skin and tighten the muscles below. This in turn reduces the therapy time required to re-educate the muscles and produces visible improvements much more quickly than conventional microcurrent devices. In implementations having a closed-loop feedback mechanism, this may provide real-time information about the status of the tissue under therapy, and the embedded intelligent circuitry may then alter the pulse parameters accordingly. This in turn eliminates overstimulation of the skin/muscle and identifies the optimum state of the muscle under therapy.

Figure 2:
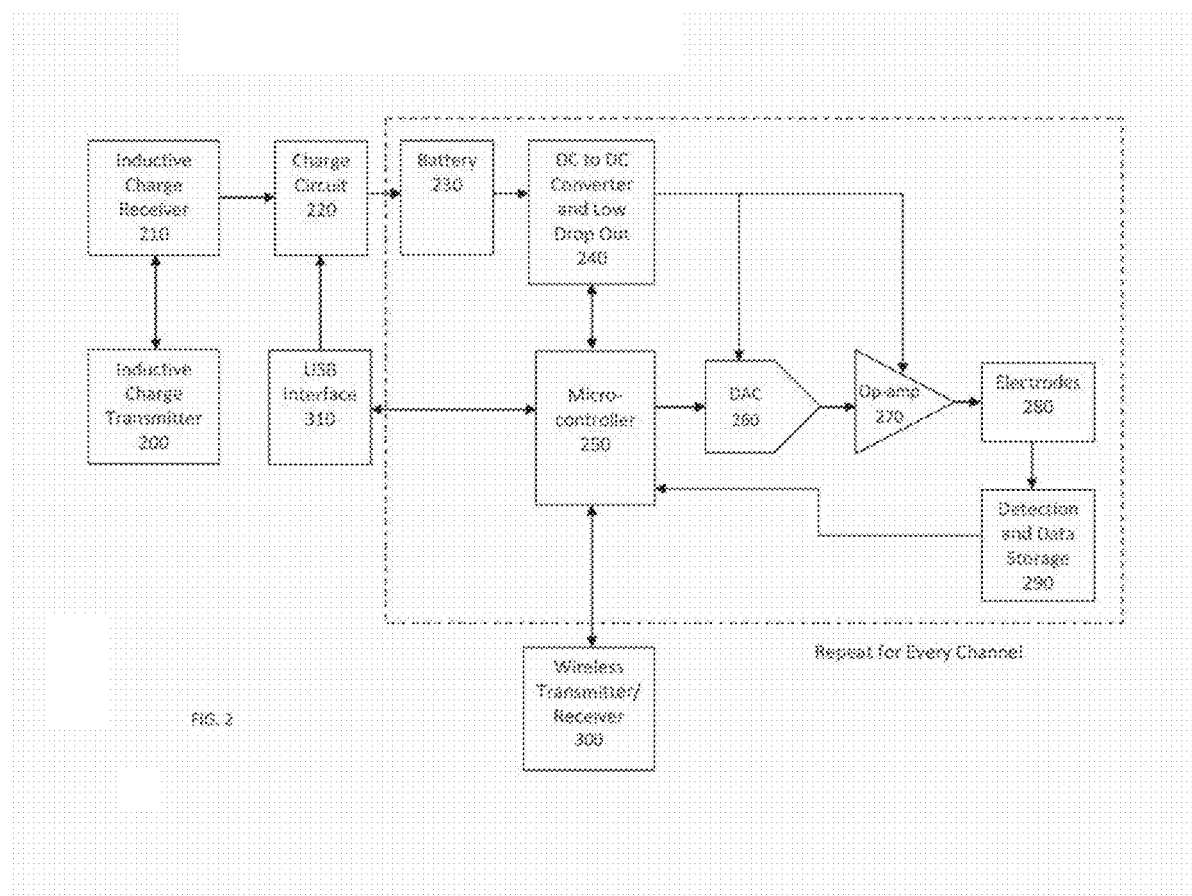
FIG. 2 is a block diagram of an example of a circuit implementation for use in an implementation of a microcurrent stimulation system.

In some implementations, the apparatus comprises an electrical current generator, closed-loop feedback sensors, and intelligent circuitry to produce various pulse waveforms. The output current is applied by using of at least two electrodes to the surface of the skin as a non-invasive method of stimulation. In a preferred embodiment, the current may be in the range of 0-500 microamperes and it flows from the first electrode through the skin and its underlying tissue and muscle, and returns from the second electrode. Pulses are generally bipolar (DC neutral) with equal amounts of electrical energy delivered both in the positive and negative directions, in order to prevent saturation of the cell membranes and resulting adverse effects. FIG. 2 shows an example of such circuit having the following components: an inductive charge transmitter 200, an inductive charge receiver 210, a charge circuit 220, a battery 230, a DC/DC converter and low drop out 240, a microcontroller 250, a digital to analog converter 260, an operational amplifier 270, electrodes 280, a detection and data storage module 290, a wireless transmitter/receiver 300, and a USB interface 310. In some implementations, the output stage may have multiple channels for stimulating multiple sites simultaneously.

The electrical properties of a human body, for example, conductance, impedance, etc., are such that low frequency pulses affect the skin, while high frequency pulses penetrate the skin and reach the underlying fat mantel and muscles. Most portable microcurrent devices operate at a single frequency and only allow the user to change the current intensity. Tabletop devices allow the output frequently to be chosen by the user in the range of 5-200 Hz. Since skin responds to lower frequencies and muscle responds to higher frequencies, current products require knowledge of different frequencies and settings that results in longer treatment sessions to stimulate both.

Figures 3A, 3B, 3C:
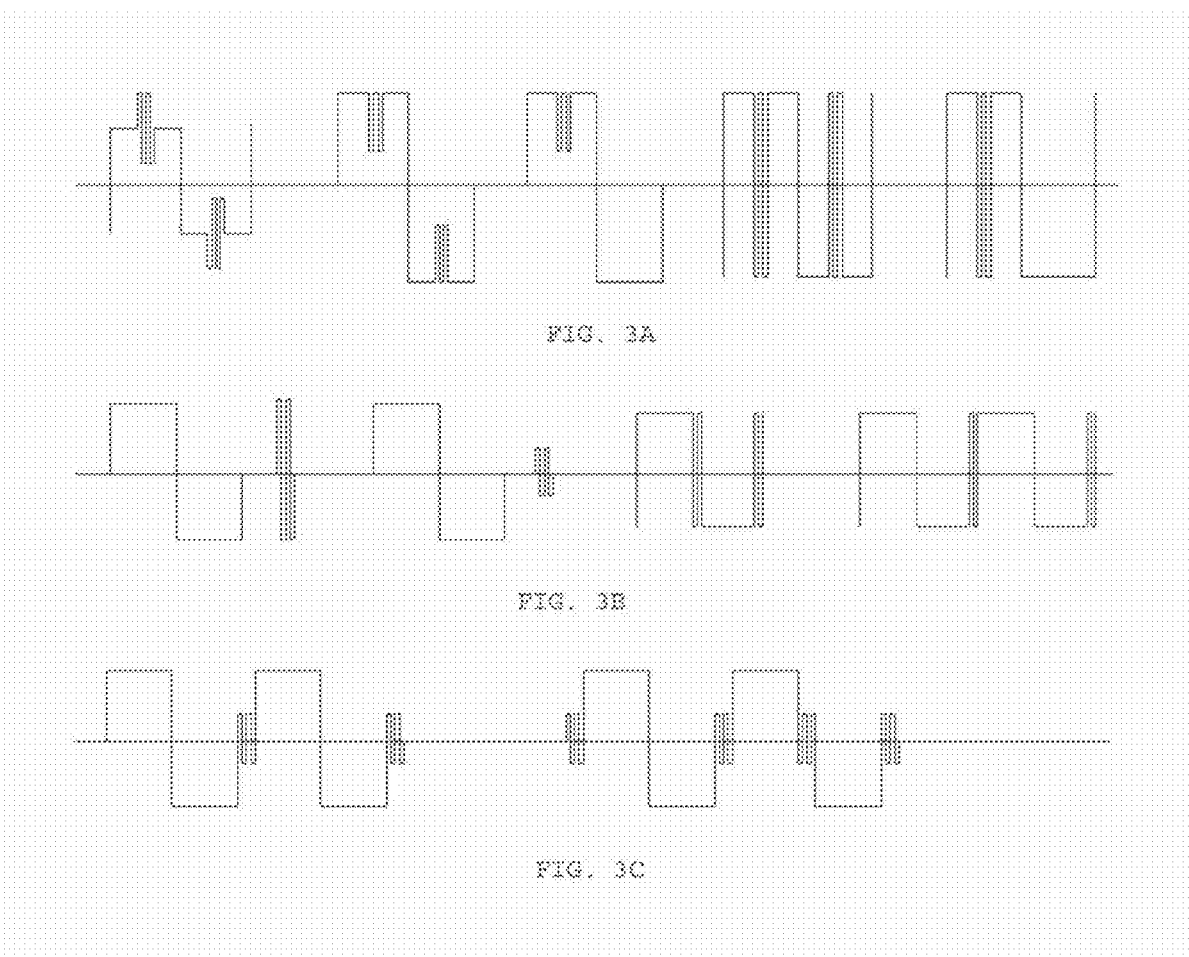
FIGS. 3A-C provide examples of electromagnetic waveforms as emitted by implementations of a microcurrent stimulation system.

In one implementation of the system disclosed herein, the device operates in mixed-mode output, producing high-frequency pulses that are superimposed on low-frequency pulses, thus providing simultaneous treatment of both the skin and the underlying muscle within one session. FIGS. 3A-C provide some examples of possible waveforms emitted by implementations of the microcurrent stimulation system, however, one of ordinary skill in the art would understand that any other appropriate waveforms may also be utilized.

In some implementations, the circuitry is housed in a self-contained enclosure that includes either a local power supply or is configured to receive power from a remote source. By non-limiting example, the power source may be a primary cell battery or a secondary cell, or any other appropriate manner of storing energy such us a capacitor, which may be replenished by the use of a directly connected external power supply. Alternately, a non-contact methodology such as induction, radio frequency or other suitable non-contact method for transferring energy may be used to replenish the built-in energy storage. In yet another embodiment, the apparatus may be powered directly using a non-contact energy transfer method, without the need for a built-in energy storage device.

In one embodiment, the output of the apparatus maybe controlled by a microprocessor and a digital to analog converter, and therefore can provide waveforms of arbitrary shape and polarity. Alternately, a digital signal processor or other circuit means maybe employed to generate those waveforms.

In some implementations, a closed-loop feedback circuit is employed to continuously monitor the stimulus pulses as they are being applied to the subject. The closed-loop feedback circuit has the capability to measure various physiological parameters in biological tissues, such as for example, the skin, the underlying fat mantel, and the muscle tissue. These parameters provide useful information about the status of the skin under treatment, enabling the Adaptive Stimulation Algorithm (ASA) that is implemented in software/firmware to determine the best course of treatment by adjusting the pulse parameters (signal rise and fall times, period, amplitude, repetition), as delivered at the electrode tips. This in turn maximizes the effectiveness of the therapy while minimizing the unpleasant sensations of electrical stimulation to the user, thereby minimizing the duration and frequency of the treatment, and eliminating unnecessary treatment.

Research data shows that human skin and muscle tissues change their shape and elasticity when stimulated by appropriate electrical signals. Furthermore, the electrical stimulus promotes several factors contributing to better skin and muscle heath through increased collagen production, hydration, increased nutrient absorption, and tissue regeneration. This change, herein referred to as Physiological Modulus (PM), can be measured through the electrical properties of these tissues. One way in which the change in PM can be detected is by measuring the total tissue impedance at various frequencies (total tissue impedance is the equivalent series and parallel resistance and capacitance of the skin and muscle tissues).

Implementations of the system and methods disclosed heroin may utilize an Adaptive Stimulation Algorithm (ASA) which is a computerized method stored in a memory that is operable as a computer software program that determines the optimal output waveform by measuring PM during the course of treatment. A course of treatment may be short-term (while the treatment is taking place), or long-term (over several days or weeks). The software may reside on a computer that is remotely communicating with the microcurrent stimulation system or programmed into the onboard memory within the device itself.

In some implementations, the current sense (CS) circuit operates by monitoring the electrical current between the two or more electrodes. A very small stimulus current is sent through the electrodes at regular intervals, and the feedback signal is monitored for contact detection. Once contact is made with the skin the current flows through a sense resistor, thus producing a voltage drop that is linearly proportional to current, and if the voltage drop measured across the resistor matches the intended current setting of the source, it is an indication that good contact with skin tissue has been established. Upon such successful contact detection the microprocessor starts applying the therapeutic stimuli. This technique allows for an automatic on/off mechanism that prolongs battery life, in portable instruments. The source current is typically applied as short bursts of micro-amp range pulses at intervals of 100 msec to 1 sec, thus using very little energy however, one of ordinary skill in the art would recognize that an appropriate range or interval of pulses may be used.

Figure 4:
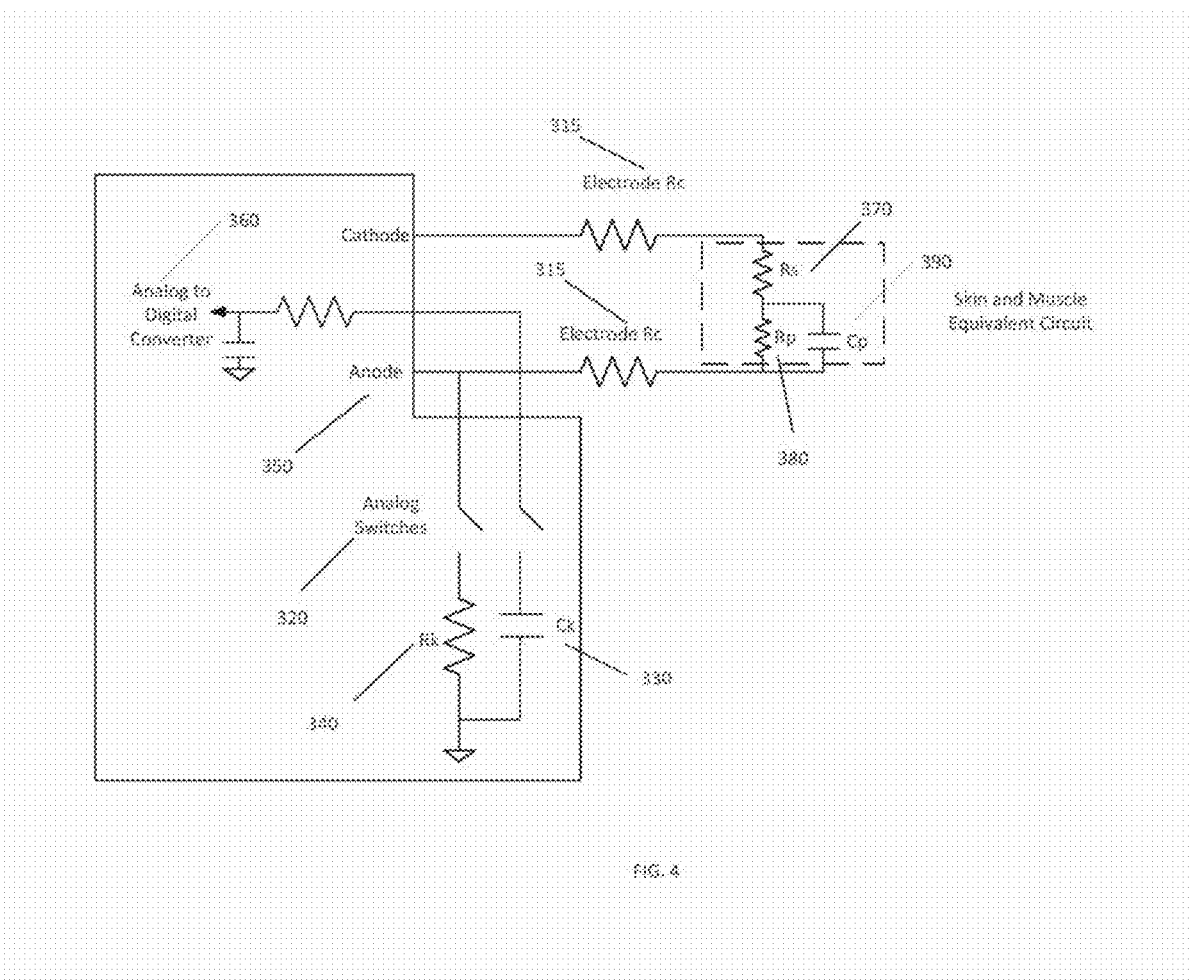
FIG. 4 is an example of a circuit for measuring impedance.

In some implementations, the microcurrent stimulation system may comprise an impedance measurement circuit that measures the PM of the skin and muscle between the electrodes, an example of which is shown in FIG. 4. The measurement may be performed at varying stimulus frequencies to capture specific tissue response (e.g. surface versus subcutaneous).

The stimulus pulses that result in Action Potential (AP) produce a physiological change in the cell tissue, resulting in increased Adenosinetriphosphate (ATP) and natural production of collagen, increased Iontophoresis for nutrient absorption, increased length and number of elastin fibers, and increased protein synthesis. This collective change is referred to as Physiological Modulus (PM). Over time, PM can be electrically measured as the change in tissue impedance (collective resistance and capacitance of skin cell tissue). The impedance (Z) measured by the electrodes is as follows:

$$Z = R_C + R_S + R_P || C_P$$

Where:
$R_C$=Contact resistance for the two electrodes
$R_S$=Skin and muscle series resistance
$R_P$=Skin and muscle parallel resistance
$C_P$=Skin and muscle parallel capacitance First, contact resistance $R_C$ 315 is measured by placing the two electrodes adjacent to each other on the skin so that they are touching one another. This eliminates $R_S$ 370, $R_P$ 380, and $C_P$ 390 from the above equation, since they are shorted out (zero ohms across $R_S$ 370, $R^P$ 380, and $C_P$ 390).

The circuit utilizes a set of semiconductor analog switches 320 to add additional "know" capacitors and resistors (built into the circuit board, hereby referred to as $C_K$ 330 and $R_K$ 340, respectively) in order to measure $R_S$ 370, $R_P$ 380, and $C_P$ 390 as follows (the resistance of the analog switch is known and is considered to be part of $R_K$ 340):

First, the electrodes are held at a known distance by utilizing some type of a mechanical fixture or clamp, and placed on the skin where measurement is to be taken.

Next, $R_K$ 340 is added between anode 350 and around by activating the corresponding analog switch 320. A DC stimulus (e.g. 10V) is applied to the skin and the voltage across $R_K$ 340 is measured by the analog to digital converter (ADC) 360. The voltage divider created by the series resistors $R_C$ 315, $R_S$ 370, $R_P$ 380, and $R_K$ 340 results in as voltage that is less than 10V. Since $R_C$ and $R_K$ are known, $R_S+R_P$ can be calculated.

Next, $R_K$ 340 is removed and $C_K$ 330 is added between the anode 350 and ground. A high-frequency AC stimulus input (e.g. 22 KHz) is applied to the skin. At high frequencies, $C_P$ 390 and $C_K$ 330 act as resistive loads, resulting in another voltage divider circuit that can be used to calculate $C_P$ 390 (some low-pass filtering may be required in order for accurate voltage measurement by the ADC 360). This technique provides is very accurate capacitance measurement circuit capable of detecting small changes in the order of 10-100 picofarads, as $C_P$ 390 changes upon application of microcurrent therapy.

PM data may then be converted to an array of binary numbers through an analog-to-digital converter, and subsequently processed by ASA software running on computerized hardware based on prerecorded correlation values. Correlation of the PM data to the subjects' state of health may be established through a database 400 that is compiled from numerous subjects of both genders and from various age groups and genetic and ethnic backgrounds. The subjects' goal is to achieve an optimal state of health as defined by aesthetic improvement of the subject to his/her own optimal natural state through visual observation made by those skilled in the art.

Day-to-day variation of a subject's skin depends on diet and environmental conditions. Therefore, it is not possible to use a fixed set of stimulus values for treatment. Also, it is not possible for the person administering the treatment to fully know the physiological change in the subject's skin on daily basis, thus choosing the optimum stimulation intensity (one that produces the fastest results with minimum discomfort) is impossible. This in turn requires an iterative process in which the clinician has to adjust various pulse parameters while asking for verbal feedback from the subject, and possibly ending up by under- or over-stimulating the skin. Over-stimulation of the skin results in undesirable health effects in the long run while under-stimulating the skin simply prolongs the treatment and wastes client's money.

Implementations of the system and methods disclosed herein overcome the above limitations by employing an Adaptive Stimulation Algorithm (ASA) that is capable of adapting the circuit output to new conditions as needed. Daily variation of the skin poses different initial conditions in the below equations (the values of $R_S$, $R_P$ and $C_P$ change daily, or even hourly, for each subject), resulting in different voltage readings.

$R_S$, $R_P$ and $C_P$ are in turn dependent on the cell's physiological state at any given time. For example, hydrated cells have an overall lower resistance. Likewise, presence of minerals and salts in the diet promotes cell heath and aid the ionic/electrical transfer between the intracellular and extracellular layers, also changing the resistance and capacitance of the cell tissue.

ASA is built around a database that contains the "relative" change of impedance. The database contains a matrix of impedance values collected during clinical trials, and is stored in the computer memory and is readily available for real-time processing of stimulus pulses. Upon initiation of a new therapy session, the electrodes are placed on the subject's skin and a new impedance measurement is taken. The algorithm then searches the database for the closest initial-condition match (static readings) and proceeds with generating the output stimuli comparable to those of the clinical data (dynamic readings). This technique results in an efficient stimulus generation without manually tweaking the instrument settings.

Figure 5:
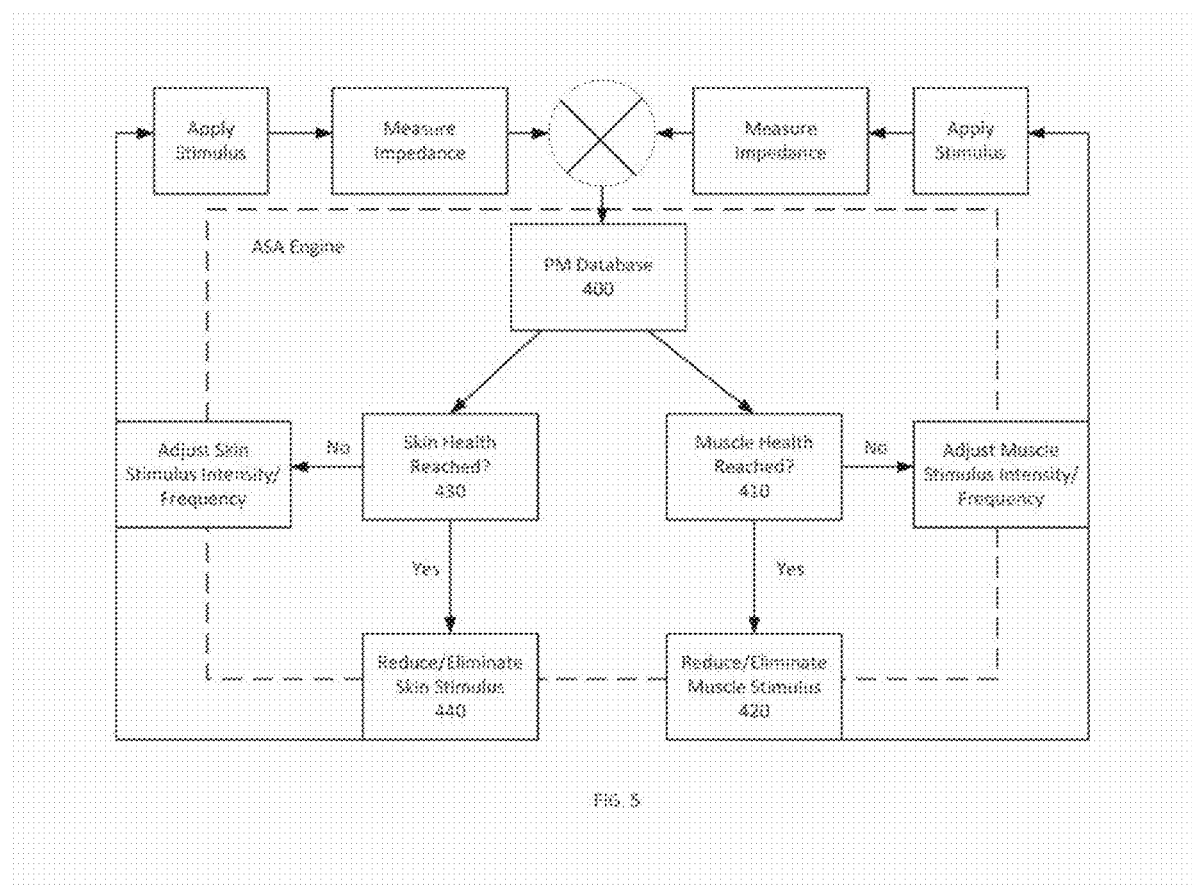
FIG. 5 is a block diagram of logic flow of a method of microcurrent stimulation.

In some implementations, the PM data array may form an input to the ASA, which in turn processes this data through both linear and nonlinear functions according to its database, and produces an output waveform that is of optimal intensity and frequency for the particular subject at his/her state of health. For example, once a subject's optimal muscle tone is reached 410 as shown in the decision logic flowchart of FIG. 5, the ASA reduces or eliminates 420 the high frequency component of the waveform. Likewise, if the skin impedance is determined to be at or near optimal value 430, but the underlying muscle is yet to be improved, the ASA reduces the low-frequency stimulus intensity 440 and increases the high-frequency stimulus.

In some implementations, the feedback circuitry also provides a way of enabling automatic power on and off based on measurements made at the electrode tips in lieu of a physical on/off switch. This function maybe accomplished by periodically powering on the output stage of the apparatus, delivering a signal and measuring the response. Before contacting the skin surface, the feedback loop of the stimulus circuit remains open and the current flow through the sense resistor does not follow that of the source. Once physical contact is made between the electrodes and the skin surface, the feedback loop is closed and the current flowing through the sense resistor equals that of the stimulus source. This in turn informs the microcontroller to begin delivering the therapy. Similarly, the same function can be used to turn off the apparatus power supply in order to extend the battery life, when the electrodes are no longer touching the skin.

Figure 6:
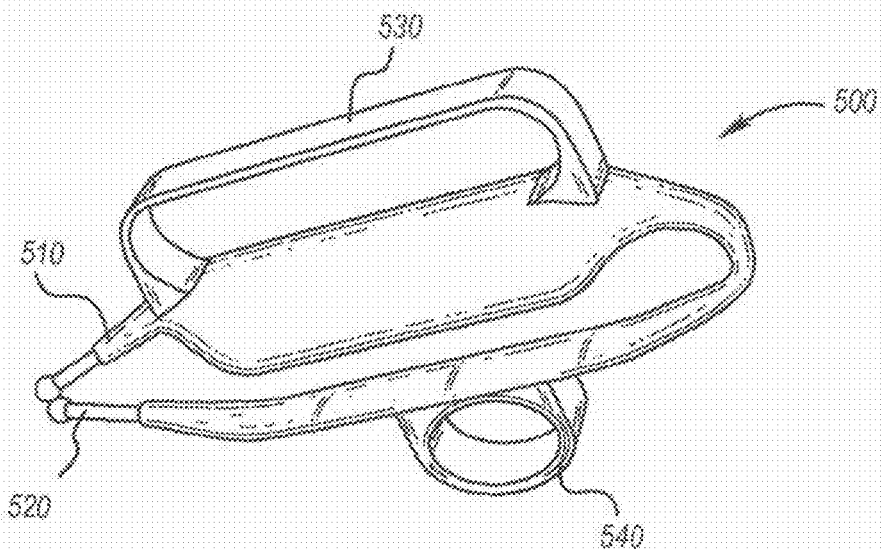
FIG. 6 is a representation of a tweezer embodiment of an implementation of a microcurrent stimulation system.

In one embodiment, the electronic circuitry and its associated power supply is enclosed in a set of handheld tweezers 500 as shown in FIG. 6. The tweezer tips 510 are comprised of electrodes 520 and the handles 530, 540 allow a user to glide the electrodes 520 along the length of the muscle.

In an alternate embodiment, the circuitry may be housed in a separate unit 600 which may be worn on the wrist or placed on a counter, and then connected to electrodes 610 using lead wires 620, or alternately by bi-directional or unidirectional wireless communication methods, such as RF, magnetic or other techniques of wirelessly transmitting energy.

Figure 7:
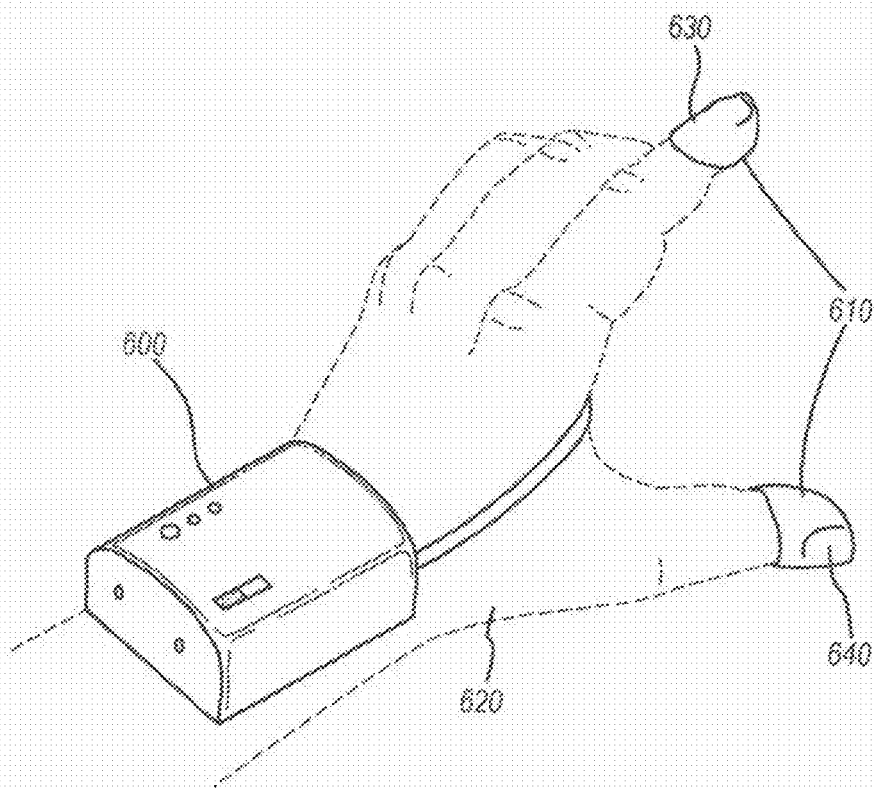
FIG. 7 is a representation of an implementation of a microcurrent stimulation system having a wrist-strapped enclosure and glove electrodes.

The electrodes may be built into a facial mask, pliable strips, finger-held applicators or fingertips on a single glove, anode 630 and cathode 640 (or vice versa), as shown in FIG. 7, which may use a conductive polymer or other suitable material such as stainless steel, copper, aluminum, titanium or any other electrically conductive material.

Figure 8:
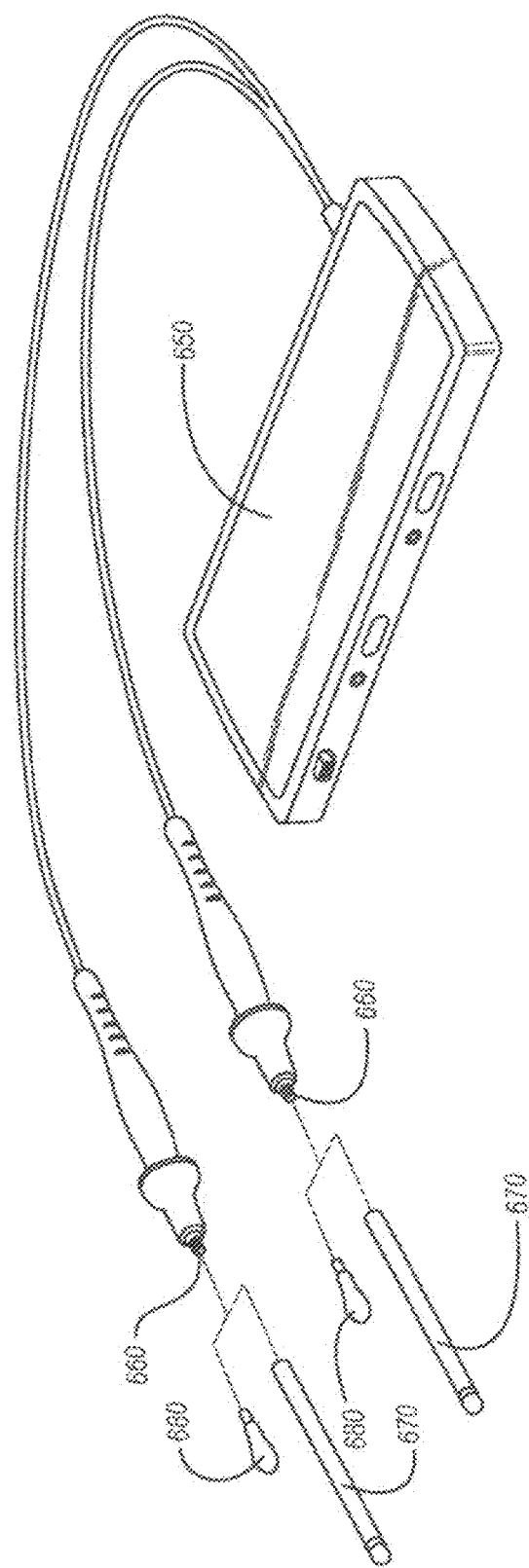
FIG. 8 is as representation of an implementation of a microcurrent system having interchangeable electrode tips.
Figure 9:
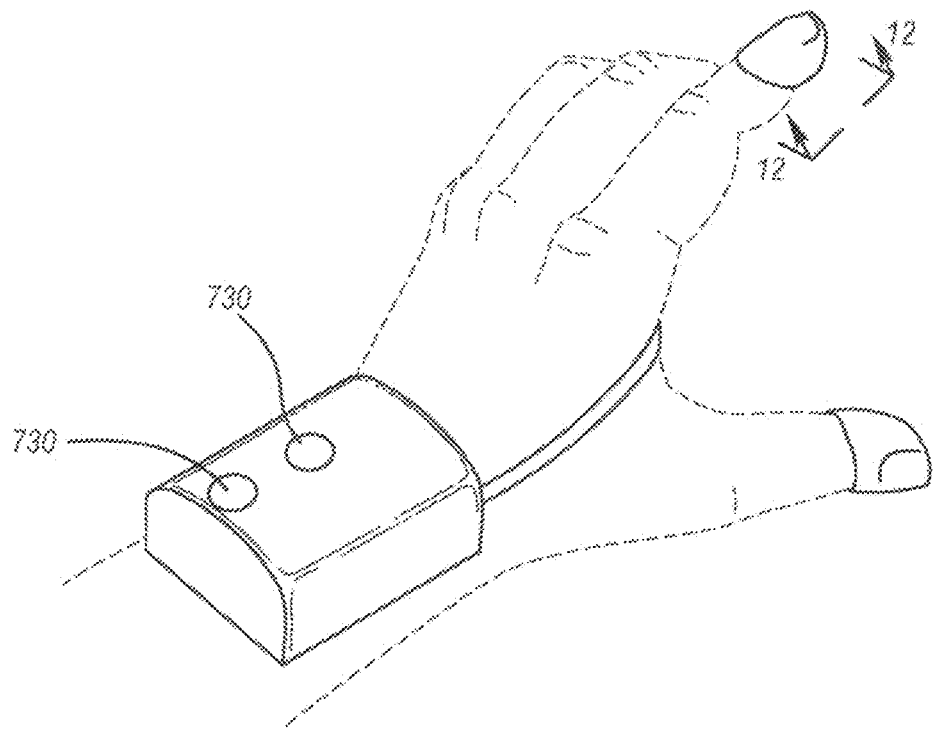
FIG. 9 is a representation of an implementation of a microcurrent stimulation system having a laser emitting device at the electrode tips.
Figure 10:
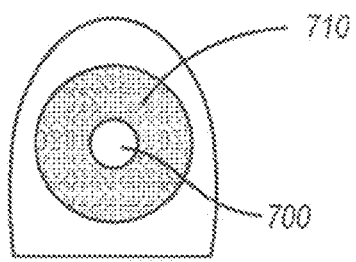
FIG. 10 is a representation of an implementation of the laser emitting device of FIG. 9.

Implementations of the device must have a minimum of two active electrodes, but may have any number of additional electrodes and stimulation channels to provide therapy to multiple locations concurrently or sequentially. In one embodiment of the sequential application, a pliable strip may be used to make contact with the skin. This strip may have a series or grid of electrodes that may be switched electrically to provide for a sequential stimulation along the length of the muscle, as is achieved by moving the electrodes by hand or using a pinching tweezer motion. The circuitry to provide this sequential stimulation may reside in the control unit itself, or maybe be built into the strip itself using a built-in de-multiplexer. The same methodology maybe used for a facial mask in order to automate the treatment without any user intervention. The electrodes may be permanently affixed to the device, or alternately, may comprise removable or interchangeable electrodes. As shown in FIG. 8, an implementation of the device 650 may have threaded probe tips 660 to allow for differently shaped electrodes to be interchanged. Electrodes may be rod-shaped 670, cotton tipped 680, round, disc-shaped, or any other shape that one of ordinary skill in the art would recognize. Some implementations use conductive polymer electrodes, but other suitable materials, such as for example, stainless steel, may also be used.

Figure 11:
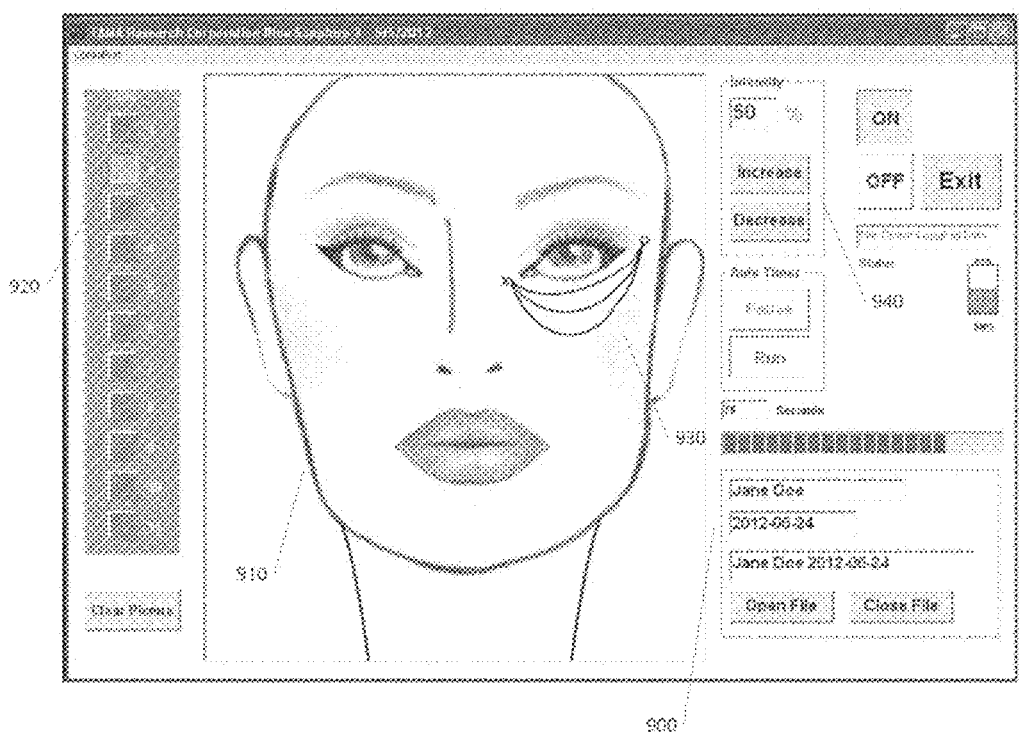
FIG. 11 provides an example of an implementation of the system having a user interface displayed on a computerized device.
Figure 12:
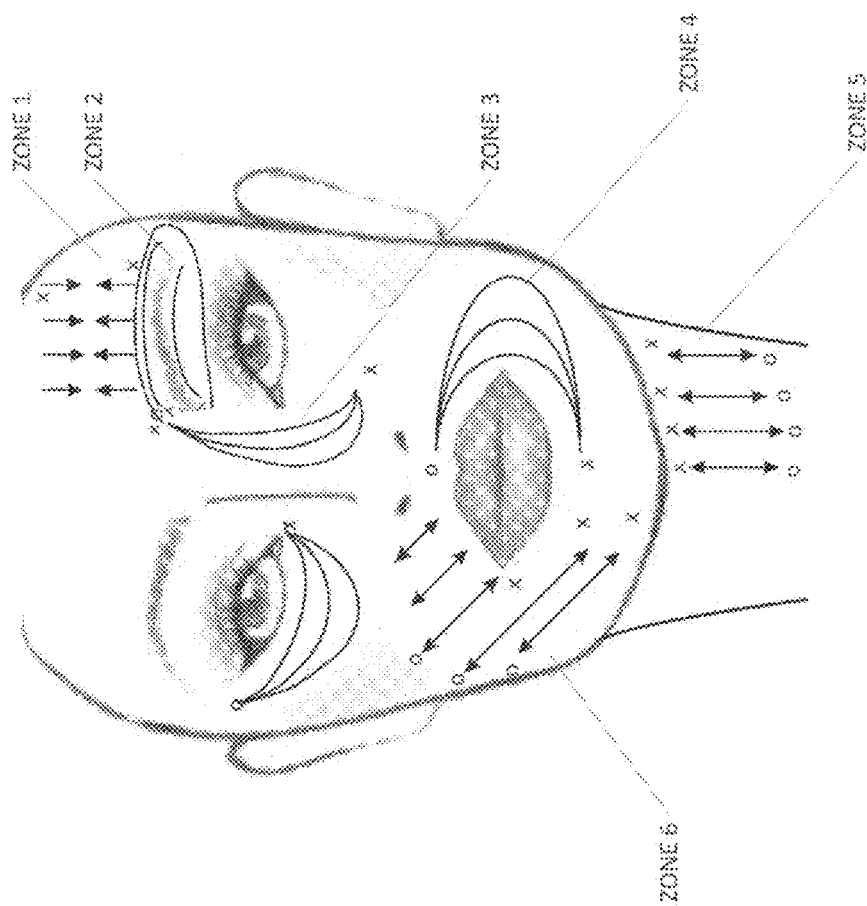
FIG. 12 is a diagram showing exemplary facial zones for microcurrent treatment.

In an alternate embodiment, electrodes 710 may be combined with a red light emitting diode (LED) or laser 700 (as shown in FIGS. 11-12) with a wavelength of about 670 nm in order to utilize the therapeutic effects of red light while microcurrent treatment is being administered. The LEDs or lasers 700 may be combined with any of the electrode configurations, such as a finger-held applicator or finger glove as shown in FIG. 11, facial mask, wired or wireless electrodes, tweezers tips or any other electrode configuration. Implementations of the device may also allow the user to turn the microcurrent and LED or laser on or off individually through the use of buttons 730, switches, or any other appropriate methodology. While a preferred embodiment may utilize a red LED, laser, or other light, it is also contemplated that any other color of light that offers bio-stimulating effects may also be used.

In one embodiment, the device includes a wireless communications feature, such as Bluetooth® or other suitable methodology, to enable bi-directional communications with a computer, smartphone or other suitable device in order to share treatment information with a local application, remote server or other software or hardware based service. For the server-based feedback embodiment, the communications may use Internet, short message service (SMS), or other means of transmitting data to and from the server. In one embodiment of the wireless communications feature, the local application or the server may determine recommended treatment patterns. In yet another embodiment, additional information may be processed and or transferred to allow for the tracking and documentation of the course of treatment.

FIG. 11 provides an example of a screen shot of a display showing a user interface provided by an implementation of the system. The user interface may display information such as, but not limited to, a user's identification information 900 and any other information that may be relevant to the user or selected treatment. Additionally, the desired area of treatment may be selected on the diagram 910 of a portion of a user's body, such as the user's face, shown on the display as a result of a user input by selecting a zone selection box 920 or area of the face 930 through the use of a touchscreen, mouse, or other input device. An example of such zones is indicated in the diagram of FIG. 12. A user may control the intensity of the treatment by selecting clicking or otherwise selecting the intensity adjustment 940 or increase and decrease buttons shown on the display. Implementations of the user display may also allow a user to select from automatically timed sessions which may be started, stopped, and/or paused by a user through a user input on the display.

One concern in using electronic instruments for therapeutic purposes is the potential hazards in the event of device malfunction. Device malfunction can be categorized according to two main areas or sources of malfunction. Implementations of the device and methods disclosed herein may employ two separate and distinct techniques for insuring that neither failure mode leads to harming the end user.

The first category of device malfunction is caused by the failure of individual components, which may result in excessive stimulus current being applied through the electrodes. This failure is prevented by running a supervisory software program in the on-board microcontroller. The microcontroller constantly monitors the current consumption of key components in the circuit (e.g. DC-DC converter, probe current draw, voltage regulator) by employing current sense circuitry. In the event excessive current draw is detected in a particular component (hence indicating malfunction), the microcontroller shuts down that portion of the circuit and turns the output off.

Figure 13:
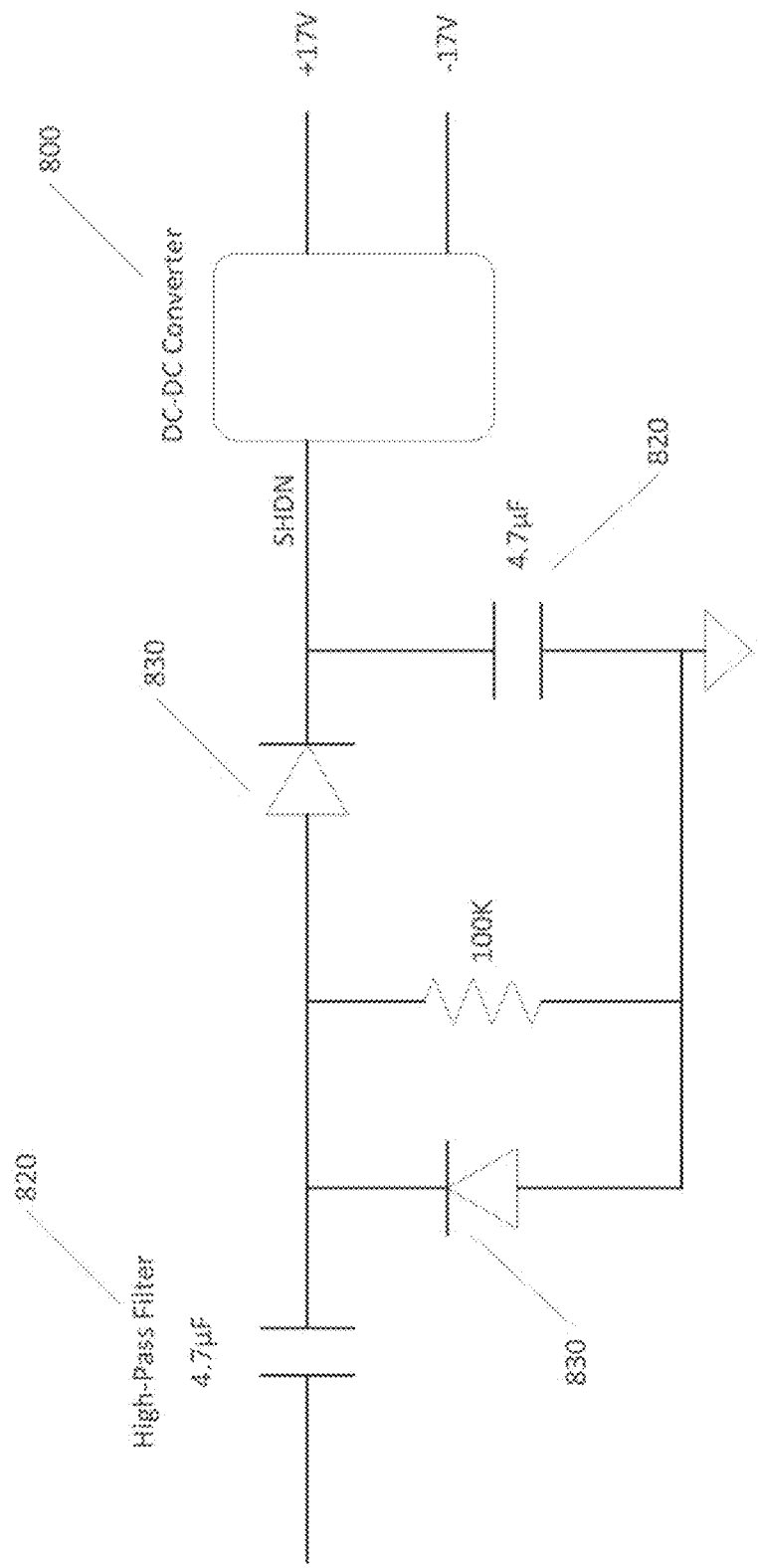
FIG. 13 is a circuit diagram of an example of a safety circuit for use in an implementation of a microcurrent stimulation system.

The second category of failure relates to the supervisory circuit (i.e. the microcontroller and the firmware). The microcontroller itself is monitored by a watchdog circuit that needs periodic refreshing. The firmware is written in a manner that at regular intervals, the watchdog register is refreshed. In the event a firmware malfunction occurs (also referred to as CPU crash), the refresh signal is not issued at the right time and the watchdog resets the microcontroller circuitry, thus bringing it back to normal operation from a clean start. This technique ensures that the microcontroller is constantly running and monitoring the output circuit, which in turn allows for shutting off the output should a component failure take place. Occasionally, the microcontroller may crash in a mode that is unrecoverable by the watchdog, while the output stimulus is latched at a high level. In this case, the microcontroller is no longer capable of turning the output off, allowing for the possibility of excessive current being applied to the subject. To prevent this scenario, a second safety mechanism is implemented, an example of which circuitry, is shown in FIG. 13.

In the exemplary implementation shown, the output circuit requires ±17 volts to operate (for sending stimulus pulses through the electrodes). This voltage is supplied by a DC-DC converter 800 that runs from the main power source in the instrument (e.g. the battery). The shutdown pin (SHDN) uses a continuous logic high signal (e.g. 3.3V) to remain active. If the voltage on this pin drops below 0.5V, the DC-DC converter circuit shuts down and the output voltage drops from ±17 volts to zero. This in turn shuts down the output current and acts as a safety for the user against possible injury. Under normal supervisory conditions, if a malfunction is detected in the DC-DC circuit (through the current sense mechanism mentioned above), the microcontroller shuts down the output by forcing SHDN to a low state. Furthermore, embodiments described in this disclosure may employ a high pass filter 820 along with appropriate level-shifting diodes 830 to create what is herein referred to as a "heartbeat monitor." The input to the filter 820 is a periodic pulse burst coming from the microcontroller (hence the term heartbeat). This pulse burst is specifically driven by firmware in a continuous loop, as opposed to driving it from a built-in hardware timer (the former ensures that in case of a crash the heartbeat stops, whereas the later may continue to produce the pulse bursts since the timer is an independent free running hardware register within the microcontroller). Using this technique, the SHDN pin is kept at a high logic state as long as the pulse stream at the input of the high-pass filter 820 is present (e.g. every 200 msec). One aspect of novelty of this implementation is in that if the microcontroller crashes beyond recovery, resulting in the heartbeat output that may be latched up at a level anywhere from 0 to VDD voltage, the SHDN pin is forced to a low state, thus shutting down the DC-DC converter 800. In other words, the DC-DC converter 800 requires an active AC pulse to remain alive. Any DC voltage for prolonged periods (e.g. beyond 200 msec) will cause it to shut down.

In places where the description above refers to particular implementations of microcurrent stimulation systems and methods, it should be readily apparent that a number of modification may be made without departing from the spirit thereof and that these implementations may be applied to other microcurrent stimulation system and method implementations.

The invention claimed is:

1. A microcurrent stimulation device comprising:
a power supply;
two or more electrodes electronically coupled to the power supply;
a microcontroller configured to generate an electromagnetic waveform comprising a plurality of high frequency alternating current pulses superimposed on a low frequency alternating current signal.

2. The microcurrent stimulation device of claim 1, wherein the microcurrent stimulation device is configured to deliver the plurality of high frequency alternating current pulses and the low frequency alternating current signal at adjustable amplitudes irrespective of previous pulses.

3. The microcurrent stimulation device of claim 1, wherein the microcontroller is further configured to generate a plurality of electromagnetic waveforms of both high and low varying frequencies.

4. The microcurrent stimulation device of claim 1, wherein the microcontroller is further configured to generate a plurality of electromagnetic waveforms of both high and low frequencies of varying amplitudes.

5. The microcurrent stimulation device of claim 1, further configured to adjust at least one of a frequency and amplitude of the electromagnetic waveform generated by the microcontroller in response to a measured electrical impedance of one or more biological tissues between the two or more electrodes.

6. The microcurrent stimulation device of claim 5, further comprising a memory configured to store information related to one or more physiological characteristics of the one or more biological tissues and wherein the microcurrent stimulation device is further configured to determine a frequency and amplitude of the electromagnetic waveform based at least partly upon the stored information.

7. A method of microcurrent stimulation comprising:
electronically coupling two or more electrodes to a power supply; and
generating an electromagnetic waveform using a microcontroller, the electromagnetic waveform comprising a continuous plurality of high frequency pulses superimposed on each of a continuous plurality of low frequency pulses.

8. The method of claim 7, further comprising measuring electrical impedance of one or more biological tissues between the two or more electrodes using an impedance measurement module.

9. The method of claim 7, wherein the high frequency component comprises high frequency pulses and the low frequency component comprises low frequency pulses.

10. The method of claim 7, further comprising generating a plurality of electromagnetic waveforms of both high and low varying frequencies using the microcontroller.

11. The method of claim 7, further comprising generating a plurality of electromagnetic waveforms of both high and low frequencies of varying amplitudes using the microcontroller.

12. The method of claim 7, further comprising adjusting at least one of a frequency and amplitude of the electromagnetic waveform generated by the microcontroller in response to a measured electrical impedance of one or more biological tissues between the two or more electrodes.

13. The method of claim 7, further comprising:
storing in a memory information related to one or more physiological characteristics of the one or more biological tissues; and
determining a frequency and amplitude of the electromagnetic waveform based at least partly upon the stored information.

14. The method of claim 7, further comprising simultaneously stimulating both skin and underlying muscle through placement of the two or more electrodes on the skin while the electromagnetic waveform is generated.

15. The method of claim 7, further comprising applying at least two, of the two or more electrodes, adjacent to each other on a patient's skin so that they are touching one another and are shorted out and measuring a contact resistance.

16. The method of claim 7, further comprising measuring a patient's physiological modulus during a first session, selecting an optimal output waveform to use as the electromagnetic waveform to generate, and changing the optimal output waveform to use as the electromagnetic waveform to generate during a second session in response to the patient's physiological modulus measured during the first session and stored in memory associated with the microcontroller.

17. The method of claim 16, wherein measuring the physiological modulus comprises measuring total tissue impedance at various frequencies.

18. A microcurrent stimulation device comprising:
a power supply;
two or more electrodes electronically coupled to the power supply;
a microcontroller configured to generate an electromagnetic waveform comprising a plurality of high frequency alternating current pulses superimposed on a continuous low frequency alternating current signal.

19. The microcurrent stimulation device of claim 18, wherein the microcurrent stimulation device is configured to deliver the plurality of high frequency alternating current pulses at variable amplitudes irrespective of an amplitude of the low frequency alternating current signal.

20. The microcurrent stimulation device of claim 18, further configured to adjust at least one of a frequency and amplitude of the electromagnetic waveform generated by the microcontroller in response to a measured electrical impedance of one or more biological tissues between the two or more electrodes.

* * * * *

UNITED STATES PATENT AND TRADEMARK OFFICE
CERTIFICATE OF CORRECTION

PATENT NO.        : 9,333,346 B1
APPLICATION NO.   : 14/283125
DATED             : May 10, 2016
INVENTOR(S)       : Ali Shambayati Page 1 of 1

It is certified that error appears in the above-identified patent and that said Letters Patent is hereby corrected as shown below:

In the specification

Column 7 line 18 of the patent it reads "heroin" it should read -- herein --.

Column 8 line 7 of the patent has the formula "$R^p$" it should read -- $R_p$ --.

Column 8 line 17 of the patent it reads "around" it should read -- ground --.

Signed and Sealed this
Twenty-first Day of June, 2016

Michelle K. Lee
*Director of the United States Patent and Trademark Office*